US012036555B2

United States Patent
Wu et al.

(10) Patent No.: US 12,036,555 B2
(45) Date of Patent: Jul. 16, 2024

(54) MICROFLUIDIC PARTICLE SORTING APPARATUS AND MANUFACTURING METHOD THEREOF

(71) Applicant: BOE TECHNOLOGY GROUP CO., LTD., Beijing (CN)

(72) Inventors: Zhihong Wu, Beijing (CN); Defeng Mao, Beijing (CN); Zijian Zhao, Beijing (CN); Yudan Yin, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 17/736,817

(22) Filed: May 4, 2022

(65) Prior Publication Data

US 2022/0258163 A1 Aug. 18, 2022

Related U.S. Application Data

(63) Continuation of application No. 16/624,813, filed on Dec. 19, 2019, now Pat. No. 11,338,292, which is a
(Continued)

(30) Foreign Application Priority Data

Sep. 26, 2018 (CN) .......................... 201811123707.6

(51) Int. Cl.
*B01L 3/00* (2006.01)
*B32B 3/30* (2006.01)
*B32B 37/18* (2006.01)

(52) U.S. Cl.
CPC .......... *B01L 3/502761* (2013.01); *B32B 3/30* (2013.01); *B32B 37/18* (2013.01);
(Continued)

(58) Field of Classification Search
CPC ......... B01L 2200/0652; B01L 2200/16; B01L 3/502761; B01L 2200/027; B01L 2200/12; B32B 3/30; B32B 37/18
See application file for complete search history.

(56) References Cited

U.S. PATENT DOCUMENTS 9,846,157 B2 12/2017 Hahn et al.
11,338,292 B2 * 5/2022 Wu ................... B01L 3/502761
(Continued)

FOREIGN PATENT DOCUMENTS

CN 103834558 A 6/2014
CN 108103022 A 6/2018

OTHER PUBLICATIONS

International Search Report Issued in Application No. PCT/CN2019/077825 dated Jun. 20, 2019, (10p).
(Continued)

*Primary Examiner* — Brian J. Sines
(74) *Attorney, Agent, or Firm* — Arch & Lake LLP (57) ABSTRACT

A microfluidic particle sorting apparatus for capturing targets from fluid containing the targets is disclosed. The apparatus includes an inlet for receiving the fluid; a sorting chamber allowing the fluid to flow through; a first outlet for discharging the fluid after flowing through the sorting chamber; a capturing structure for capturing the cells, wherein the capturing structure is upstream of the first outlet, and includes obstacles in an array, each extending through the sorting chamber in a lateral direction with respect to a fluid flow of the fluid; and a second outlet upstream of the capturing structure comprising a plurality of openings; wherein a gap between two adjacent obstacles is equal to or greater than each opening of the second outlet.

15 Claims, 7 Drawing Sheets

Related U.S. Application Data continuation of application No. PCT/CN2019/077825, filed on Mar. 12, 2019.

(52) U.S. Cl.
  CPC .  *B01L 2200/027* (2013.01); *B01L 2200/0652* (2013.01); *B01L 2200/12* (2013.01)

(56) References Cited

U.S. PATENT DOCUMENTS

| | | |
|---|---|---|
| 2016/0139012 A1 | 9/2016 | D'Silva et al. |
| 2021/0178393 A1* | 6/2021 | Craighead ......... B01L 3/502753 |

OTHER PUBLICATIONS

Mohamed, Hisham, et al., "Isolation of Tumor Cells Using Size and Deformation," Journal of Chromatography, dated Nov. 20, 2009, No. 47, vol. 1216, (pp. 8289-8295).

\* cited by examiner

```
┌─────────────────────────────────────────────────────────┐
│ Injecting the liquid to be sorted into the sorting chamber via the sample │
│ inlet to enable the liquid to pass through the first fluid guiding structure │
│ and reach the second sample outlets and the capturing structure │
└─────────────────────────────────────────────────────────┘  S410
                            │
┌─────────────────────────────────────────────────────────┐
│       Sucking out the residue via the first sample outlet        │
└─────────────────────────────────────────────────────────┘  S420
```

MICROFLUIDIC PARTICLE SORTING APPARATUS AND MANUFACTURING METHOD THEREOF

CROSS-REFERENCE TO RELATED APPLICATIONS

The present application is a continuation application of U.S. patent application Ser. No. 16/624,813 filed on Dec. 19, 2019 which is a continuation of International Application No. PCT/CN2019/077825 filed Mar. 12, 2019 based upon and claims priority to Chinese Patent Application No. 201811123707.6, filed on Sep. 26, 2018, the entire contents of the above applications are incorporated herein by reference in their entireties for all purposes.

TECHNICAL FIELD

The present disclosure relates to the field of medical equipment, and particularly relates to, but not limited to, a microfluidic particle sorting apparatus, a method of manufacturing the apparatus, a chip for sorting target particles, a method for manufacturing the chip, a sorting system comprising the chip and a method for sorting target particles by the chip.

BACKGROUND

In order to diagnose whether a patient suffers from a cancer, it is required to conduct a tissue biopsy. Particularly, it is required to tong or cut from the patient a lesion tissue in vivo for assay, which causes pain in the patient.

With the development of medical technology, there arises the technique of extracting circulating tumor cells (CTCs) from the peripheral blood of patients to conduct liquid biopsy, which largely alleviates the pain of the patient in the examination process.

Circulating tumor cells are cells that exist in peripheral blood. There are also a large amount of karyocytes (including vascular endothelial cells, benign epithelial cells and so on) in blood. Therefore, in using the liquid biopsy technique, circulating tumor cells have to be separated from other cells and enriched before they can be identified and analyzed. A currently commonly used method for separating circulating tumor cells is sorting peripheral blood by a sorting chip, to obtain circulating tumor cells.

It is desirable to provide a chip that can separate circulating tumor cells with a high efficiency.

SUMMARY

An apparatus or chip is provided for capturing particles from fluid containing the particles. The particles, i.e. target, may be cells, or particularly, tumor cells. A method of manufacturing such apparatus or chip is also provided.

According to a first aspect of the present disclosure, there is provided a microfluidic particle sorting apparatus for capturing targets from fluid containing the targets, comprising: an inlet for receiving the fluid; a sorting chamber allowing the fluid to flow through; a first outlet for discharging the fluid after flowing through the sorting chamber; a capturing structure for capturing the cells, wherein the capturing structure is upstream of the first outlet, and comprises obstacles in an array, each extending through the sorting chamber in a lateral direction with respect to a fluid flow of the fluid; and a second outlet upstream of the capturing structure comprising a plurality of openings; wherein a gap between two adjacent obstacles is equal to or greater than each opening of the second outlet.

Optionally, the gap between two adjacent obstacles is approximately equal to a size of the cells to be captured.

Optionally, the plurality of opening of the second outlet comprises an array of holes, and the gap between two adjacent obstacles is equal to or greater than a diameter of the holes.

Optionally, the sorting chamber is between a cover layer and a sorting layer opposite to one another, the inlet and the first outlet are arranged in the cover layer, the second outlet is arranged in the sorting layer, and each of the obstacle extends from the sorting layer to the cover layer.

The apparatus may further comprise a first fluid guiding structure upstream of the second outlet for smoothing the fluid flow, the first fluid guiding structure comprising a plurality of columns, each extending from the sorting layer to the cover layer.

Optionally, the plurality of columns arranged in lines parallel to each other, a most upstream line partially along a cross section of the sorting chamber lateral to a direction of the fluid flow.

Optionally, a column in a downstream line is located corresponding to a gap in an adjacent upstream line.

Optionally, each column of the most upstream line has side surfaces parallel to the fluid flow and a cross section of each column of the most upstream line has a part of decreasing width in the direction of fluid flow.

Optionally, a distance between opposing side surfaces of adjacent columns of the most upstream line is in a range of 40 μm to 50 μm.

Optionally, a cross section of each column of the remaining lines has a part of increasing width in the direction of fluid flow.

The apparatus may further comprise a second fluid guiding structure downstream of the second outlet and upstream of the capturing structure for smoothing the fluid flow toward the capturing structure, the second fluid guiding structure comprising a second line of columns, each extending from the sorting layer to the cover layer.

Optionally, each column of the second line has side surfaces parallel to the fluid flow, and a distance between opposing side surfaces of adjacent columns of the second line is in a range of 40 μm to 50 μm.

Optionally, the array of obstacles comprises a plurality of lines of obstacles and the lines are arranged such that an obstacle of one line is at an equal distance from two adjacent obstacles of an adjacent line.

Optionally, a distance between the lines of obstacles decreases in a direction of the fluid flow, and the distance between the lines of obstacles is in the range of 5 μm to 10 μm.

Optionally, each obstacle has a triangular cross section and a vertex of the triangle points away from the direction of the fluid flow.

The apparatus may further comprise a back cover layer opposite to the sorting layer forming a second chamber with a back side of the sorting layer, wherein the sorting layer is sandwiched between the cover layer and the back cover layer, and at least one third outlet is on the back cover layer.

According to a second aspect of the present disclosure, there is provided a method for manufacturing a microfluidic particle sorting apparatus, comprising: forming a cover layer, the cover layer comprising a first opening as an inlet and a second opening as a first outlet; forming a sorting layer, the sorting layer comprising a first fluid guiding structure, a capturing structure and a second fluid guiding structure formed on a side of a substrate, and a second outlet having an opening through the substrate; and bonding the cover layer with the sorting layer to form a sorting chamber allowing a fluid containing cells to flow from the inlet to the first outlet; wherein the capturing structure for capturing cells is located upstream of the first outlet, the capturing structure comprising an array of obstacles extending through the sorting chamber in a lateral direction with respect to the fluid flow; and wherein a gap between two adjacent obstacles is equal to or greater than the opening of the second outlet.

The method may further comprise forming a back cover layer comprising an opening as a third outlet; and bonding the back cover layer with the sorting layer to form a second chamber with a back side of the sorting layer.

The method may further comprise forming a recess on the back cover layer for forming the second chamber with the back side of the sorting layer.

The method may further comprise forming a recess on the back side of the sorting layer to form the second chamber with the back cover layer.

BRIEF DESCRIPTION OF DRAWINGS

A description of the embodiments will be rendered with reference to specific embodiments illustrated in the appended drawings. Given that these drawings depict only some embodiments and are not therefore considered to be limiting in scope, the embodiments will be described and explained with additional specificity and details through the use of the accompanying drawings, in which.

DETAILED DESCRIPTION

The disclosure will be described hereinafter with reference to the accompanying drawings which illustrate embodiments of the disclosure. This disclosure may, however, be implemented in many other forms and shall not be construed as limited to the illustrated embodiments set forth herein.

The terms used herein are merely for describing specific embodiments, and are not intended to limit the disclosure. As used herein, the singular forms "a" and "an" are intended to include the plural forms as well, unless otherwise indicated clearly in the context. It is to be further understood that the terms "comprise" and/or "include" used herein indicate the presence of the described features, entirety, steps, operations, elements and/or components, but do not exclude the presence or addition of one or more other features, entirety, steps, operations, elements, components and/or combinations thereof. It should also be understood that the term "and/or" as used herein refers to and includes any and all possible combinations of one or more of the associated listed items.

In one embodiment there is provided a microfluidic cell sorting apparatus, which may be in the form of a chip for sorting target cells. The terms "microfluidic cell sorting apparatus", "chip for sorting target cells" and "chip" may be used interchangeably throughout this description. The microfluidic cell sorting apparatus is used for capturing cells, namely target cells, from fluid, such as blood that contain the cells.

Figure 1:
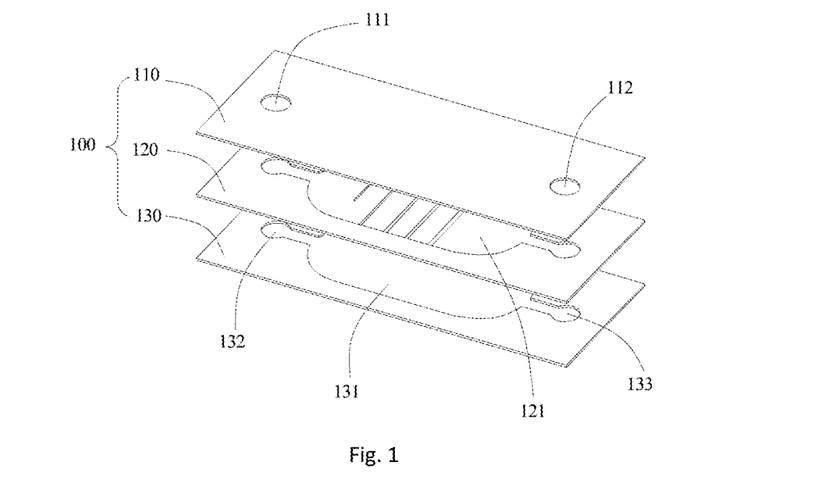
FIG. 1 is a schematic exploded view of a chip for sorting target cells according to the present disclosure.
Figure 2:
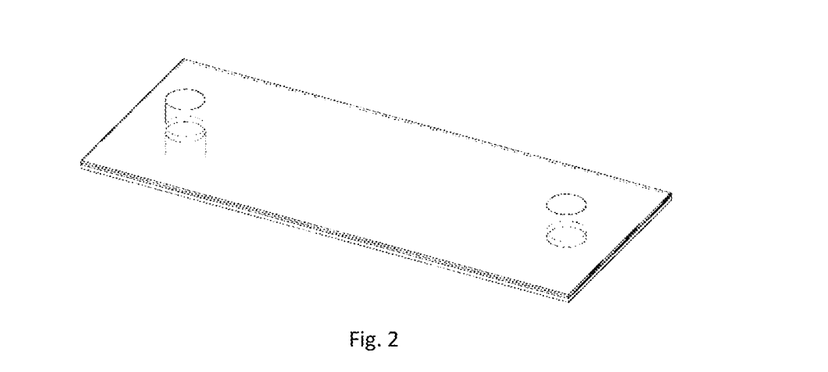
FIG. 2 is a schematic assembly view of the chip in FIG. 1.

As shown in FIGS. 1 and 2, the microfluidic particle sorting apparatus, or in this case cell sorting apparatus, may comprise: an inlet, in this example a sample inlet 111, for receiving the fluid; a sorting chamber 121 allowing the fluid to flow through; a first outlet, in this example a first sample outlet 112, for discharging the fluid after flowing through the sorting chamber 121. In one embodiment, the chip comprises a chip main body 100, a sorting chamber 121 formed in the chip main body 100, a flow guiding structure formed within the sorting chamber 121 and a capturing structure formed within the sorting chamber 121.

The chip main body 100 is provided with the sample inlet 111 that communicates with the sorting chamber 121 and the first sample outlet 112 that communicates with the sorting chamber 121.

The microfluidic cell sorting apparatus may further comprise: a capturing structure, in this example a plurality of capturing columns 126, for capturing the cells, wherein the capturing structure is upstream of the first outlet 111, and comprises an array of obstacles, namely the capturing columns 126, each extending through the sorting chamber in a lateral direction with respect to the fluid flow; and a second outlet, in this example second sample outlets 124, upstream the capturing structure; wherein a gap between two adjacent obstacles is equal to or greater than an opening of the second outlet.

Figure 3:
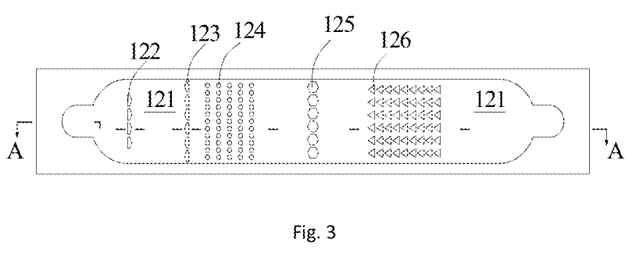
FIG. 3 is a top view of the chip in FIG. 2 in which the cover layer has been removed.
Figure 4:
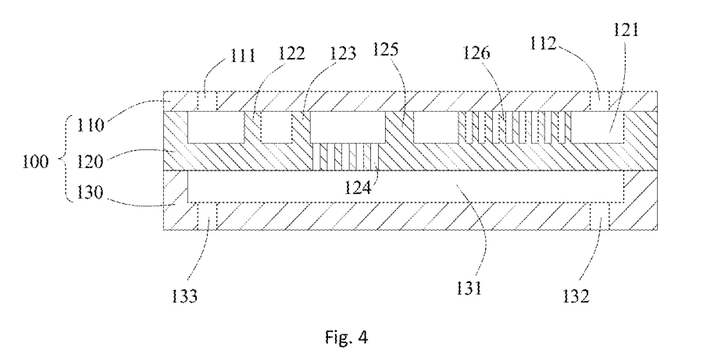
FIG. 4 is a schematic section view of the chip along line A-A in FIG. 3.

As shown in FIGS. 3 and 4, the flow guiding structure and the capturing structure are arranged sequentially between the sample inlet 111 and the first sample outlet 112, the bottom wall of the sorting chamber 121 is provided with a plurality of second sample outlets 124, and the second sample outlets 124 are located between the flow guiding structure and the capturing structure.

The flow guiding structure is used to smooth the fluid that flows from the sample inlet 111 toward the second sample outlets 124.

The opening of the second sample outlet 124 is less than a first preset value.

The capturing structure comprises a plurality of capturing columns 126 that are arranged with a gap between adjacent ones. The gap between two adjacent capturing columns 126 is not greater than a second preset value, wherein the second preset value is greater than the first preset value.

In the present disclosure, the particular numerical values of the first preset value and the second preset value may be determined according to the cells to be sorted. Particularly, the second preset value may be the size of the target cells, and the first preset value may be the size of the particles in the liquid to be sorted other than the target cells. It can be easily understood that, the size of the particles is less than the size of the target cells. In one embodiment, when the liquid to be sorted is peripheral blood and the target cells are circulating tumor cells, the first preset value may be the size of the erythrocytes or leukocytes in blood. The second preset value may also be slightly greater than the size of the target cells. In one embodiment, the gap between two adjacent capturing columns 126 is equal to or greater than the opening of the second sample outlet 124.

For example, in order to facilitate capturing the target cells, the liquid may be pre-treated. For example, microspheres are introduced, so that the microspheres adhere to the surfaces of the target cells, forming target bodies of a larger size. In such a case, the second preset value may be slightly greater than the size of the target cells.

A micropump or syringe pump may be used to inject the liquid into the sample inlet 111, and by the effect of pressure, the liquid flows from the sample inlet 111 toward the flow guiding structure, the second sample outlets 124, the capturing structure and the first sample outlet 112.

The flow of the liquid that enters the sorting chamber is regulated by the pressure and the flow guiding structure, so that the liquid can be evenly distributed within the sorting chamber. The liquid is preliminarily sorted by the second sample outlets, to separate the cells of the relatively small dimension or size from the liquid. Thereby, the flow resistance in the sorting chamber can be reduced, to improve the flux of the liquid.

By capturing the target cells of the relatively large size using the capturing structure, enrichment of the target cells can be realized. Furthermore, the cells of the relatively small size can pass through the capturing structure, and are discharged via the first sample outlet 112.

In one embodiment, the chip may be used to sort the circulating tumor cells in peripheral blood. A blood sample is injected into the sorting chamber of the chip via the sample inlet 111 using a syringe pump or peristaltic pump, the blood sample, after being smoothed by the flow guiding structure, reaches the second sample outlets 124 (the diameter of the second sample outlets 124 is greater than the size of erythrocyte and leukocyte), and a large amount of plasma, erythrocytes and leukocytes leave the sorting chamber 121 via the second sample outlets 124, thereby reducing the congestion at the capturing structure by the large amount of erythrocytes and leukocytes. The gap between the capturing columns is set to be less than the size of circulating tumor cells, and circulating tumor cells have the characteristic of not being easily deformed, so the circulating tumor cells can be stuck between the capturing columns 126. Although the sizes of leukocytes are not uniform and some leukocytes have larger sizes, leukocytes easily deform so that the pressure of the pump can enable the leukocytes to deform and pass through the gaps between the capturing columns. Accordingly, other plasma, leukocytes and erythrocytes pass through the gaps between the capturing columns 126, and are sucked out from the first sample outlet 112. Accordingly, the separating of the circulating tumor cells in the blood sample from other functional particles can be realized.

It can be easily understood that, in the present disclosure, the opening of the sample inlet 111 is greater than the opening of the second sample outlet 124, and the opening of the first sample outlet 112 is greater than the size of the second sample outlets 124. In one embodiment, the sample inlet 111 and the first sample outlet 112 comprises round holes, wherein the diameter of the sample inlet 111 may be between lmm to 1.8 mm, and similarly, the diameter of the first sample outlet 112 may also be between 1 mm to 1.8 mm.

In one embodiment, the height of the capturing columns may be between 60 μm to 100 μm. The depth of the sorting chamber may be the identical with the height of the capturing columns; that is, the depth of the sorting chamber may be between 60 μm to 100 μm.

The second sample outlets 124 may conduct preliminary separation to the liquid that enters the sorting chamber. When the target cells exist in the liquid that have been preliminarily sorted, the target cells can be trapped between the capturing columns, and the residual liquid and cells may be sucked out via the first sample outlet.

The enriching of the target cells facilitates counting under the microscope or fluorescent expression, and also facilitates observing the target cells.

In order to facilitate complete sorting of the fluid that enters the chip, the sample inlet 111 is located at one end of the sorting chamber in the longitudinal direction, and the first sample outlet 112 is located at the other end of the sorting chamber in the longitudinal direction. The plurality of second sample outlets 124 are arranged as at least one line, and the direction of the line of the second sample outlets 124 intersects the longitudinal direction of the sorting chamber.

After the liquid that enters the sorting chamber 121 passes through the flow guiding structure, the liquid fills the lateral direction of the sorting chamber. Because the aligning direction of the second sample outlets 124 intersects the longitudinal direction of the sorting chamber, when the liquid flows toward the capturing structure, it may entirely pass through the second sample outlets 124, thereby sorting more fully the fluid.

In the present disclosure, the structure of the flow guiding structure is not particularly defined. As shown in FIGS. 2 to 4, the flow guiding structure comprises at least one first-order flow guiding strip, which may be referred to as a first fluid guiding structure in the present disclosure, and the first-order flow guiding strip is provided between the sample inlet 111 and the first sample outlet 112.

The length direction of the first-order flow guiding strip intersects the longitudinal direction of the sorting chamber 121. As shown in FIG. 3, the first-order flow guiding strip comprises a plurality of first-order flow guiding columns 122 that are arranged in a line with a gap between adjacent flow guiding columns, one end of the first-order flow guiding columns 122 is fixed on the bottom wall of the sorting chamber 121, and the first-order flow guiding columns 122 protrude toward the top wall of the sorting chamber 121.

After the liquid to be detected flows from the sample inlet 111 into the sorting chamber 121, the liquid concentrates relatively under the sample inlet 111, and after the liquid flows to the first-order flow guiding strip, the plurality of first-order flow guiding columns 122 can spread the liquid, thereby enabling the liquid to more smoothly distribute within the sorting chamber 121, and avoiding the cells in the liquid from accumulating at the second sample outlets 124 and blocking the second sample outlets 124.

In order to enable the liquid to more smoothly distribute within the sorting chamber 121, as shown in FIGS. 2 to 4, the first fluid guiding structure comprises a plurality of first-order flow guiding strips (in FIG. 2, the two black lines on the left show two first-order flow guiding strips), the plurality of first-order flow guiding strips are arranged with spacing along the longitudinal direction of the sorting chamber, and two adjacent first-order flow guiding strips are parallel.

The two ends in the length direction of a first first-order flow guiding strip (shown by the most left black line in FIG. 2) in the direction from the sample inlet 111 to the first sample outlet 112 have a gap with the corresponding side wall of the sorting chamber, and the two ends in the length direction of the other first-order flow guiding strips are individually connected to the corresponding side walls of the sorting chamber. That is, the most upstream strip (the most upstream line of first-order flow guiding columns) span partially along a cross section of the sorting chamber lateral to the direction of the fluid flow; and the other strip spans across the entire cross section of the sorting chamber lateral to the direction of the fluid flow.

Because the liquid that enters via the sample inlet 111 is relatively concentratively distributed directly below the sample inlet 111, the relatively short first-order flow guiding strip realizes the preliminary dispersing of the liquid to avoid the liquid from flowing only in the middle part of the sorting chamber. Therefore, setting the first first-order flow guiding strip to be relatively short can simplify the manufacturing process.

The plurality of first-order flow guiding strips are parallel, which can prevent the liquid that flows through the flow guiding strips from generating air bubbles to enable the liquid to disperse more smoothly.

The plurality of second sample outlets may be arranged as a plurality of lines of holes, forming an array of holes, and the direction of the lines of the second sample outlets intersects the longitudinal direction of the sorting chamber.

In the present disclosure, the number of the second sample outlets is not particularly defined. In one embodiment, the second sample outlets are arranged as 4 to 8 lines. In a same line, the interval between two adjacent holes is 10 μm to 30 μm; the interval between two adjacent lines of holes is 10 μm to 30 μm; and the diameter of the holes is 5 μm to 10 μm.

Figure 5:
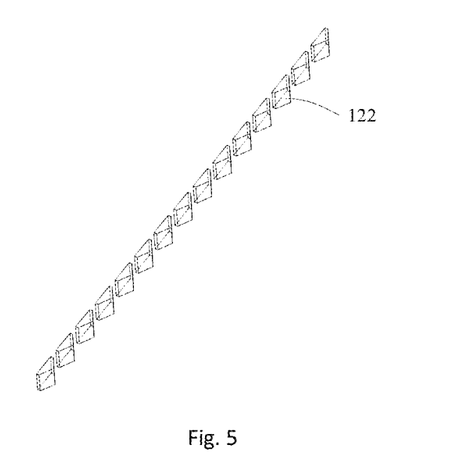
FIG. 5 is a schematic diagram of a first first-order flow guiding strip of the chip according to the present disclosure.

In one embodiment of the present disclosure, as shown in FIGS. 3 to 5, the first first-order flow guiding strip in the direction from the sample inlet 111 to the first sample outlet 112 comprises a line of first-order flow guiding columns 122, and the configuration of the first-order flow guiding columns 122 in the first first-order flow guiding strip, i.e. the most upstream line of the columns, satisfies the following conditions.

Figure 6:
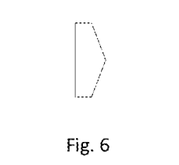
FIG. 6 is a schematic diagram of a cross section of a first-order flow guiding column of the first-order flow guiding strip shown in FIG. 5.

The cross section of each first-order flow guiding column may be a polygon (as shown in FIG. 6); each first-order flow guiding column comprises flow guiding side surfaces that are parallel, as shown in FIGS. 3 and 5; the flow guiding side surfaces of two adjacent first-order flow guiding columns are configured oppositely, the opposing flow guiding side surfaces of two adjacent first-order flow guiding columns are parallel, and the width of a part of the cross section downstream of the flow guiding side surfaces gradually decrease, i.e. the cross section of each column of the first first-order flowing guide strip has a part of decreasing width in the direction of fluid flow. In the present disclosure, the sample inlet is the upstream, and the first sample outlet is the downstream. In FIG. 6, the left side is the upstream, and the right side is the downstream.

Because the opposing side surfaces of two adjacent first-order flow guiding columns 122 are parallel, the flow rate of the fluid that passes through the gaps between two adjacent first-order flow guiding columns in the first first-order flow guiding strip almost does not change, so that the liquid that flows through the first first-order flow guiding strip does not generate air bubbles.

After the liquid flows through the parallel side surfaces, the gap between two adjacent first-order flow guiding columns gradually increases, which can enable the liquid to diffuse and expand in the lateral direction of the sorting chamber after flowing through the first first-order flow guiding strip, thereby ensuring the smooth preliminary dispersing of the liquid.

In the embodiment shown in FIG. 6, the cross section of the first-order flow guiding columns 122 is a pentagon, in which the pentagon is the combination of a rectangle and an obtuse-angle isosceles triangle, and the bottom side of the obtuse-angle isosceles triangle coincides with a long side of the rectangle. In one embodiment, the side length of the long sides of the rectangle is 80 μm to 100 μm; the side length of the short sides of the rectangle is 10 μm to 20 μm; the bottom side of the obtuse-angle isosceles triangle and a long side of the rectangle coincide and have the same length. The apex angle of the obtuse-angle isosceles triangle may be 150°, thereby avoiding generating a dead volume or air bubbles after the liquid passes through the gap between the first-order flow guiding columns 122, ensuring that the flow rate of the liquid is smooth after passing through the first first-order flow guiding strip.

In order to diffuse more smoothly the liquid that enters the sorting chamber, a second first-order flow guiding strip in the direction from the sample inlet to the first sample outlet comprises a plurality of first-order flow guiding columns 123 that are arranged as one line, and the configuration of the first-order flow guiding columns 123 in the second first-order flow guiding strip satisfies the following conditions.

Figure 7:
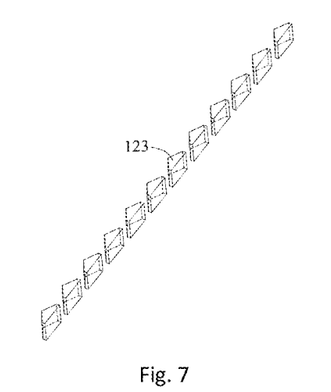
FIG. 7 is a schematic diagram of a second first-order flow guiding strip of the chip according to the present disclosure.
Figure 8:
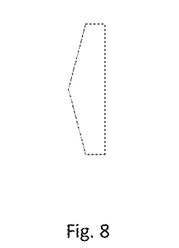
FIG. 8 is a schematic diagram of a cross section of a first-order flow guiding column of the second first-order flow guiding strip shown in FIG. 7.
Figure 9:
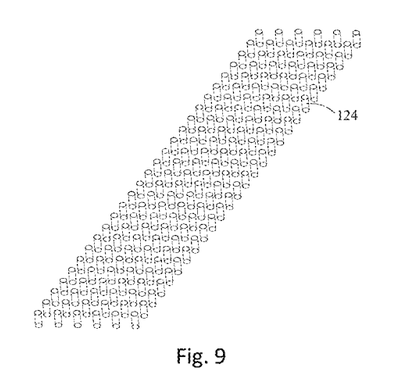
FIG. 9 is a schematic diagram of second sample outlets.

As shown in FIGS. 3 and 7, the cross section of the first-order flow guiding columns 123 is a polygon, and the side surfaces of two adjacent first-order flow guiding columns 123 are configured oppositely. As shown in FIG. 8, the width of a part of the cross section that is upstream of the parallel side surfaces gradually increases, i.e. the cross section has a part of increasing width in the direction of fluid flow.

In the embodiment shown in FIG. 8, the cross section of the first-order flow guiding columns 123 is the combination of a rectangle and an obtuse-angle isosceles triangle, in which the bottom side of the obtuse-angle isosceles triangle coincides with a long side of the rectangle. In one embodiment, the side length of the long sides of the rectangle is 80 μm to 100 μm; the side length of the short sides of the rectangle is 10 μm to 20 μm; the bottom side of the obtuse-angle isosceles triangle and a long side of the rectangle coincide and have the same length; and the apex angle of the obtuse-angle isosceles triangle may be 150°. That is, the shape of the first-order flow guiding columns 122 of the first first-order flow guiding strip and the shape of the first-order flow guiding columns 123 of the second first-order flow guiding strip are the same, but the two flow guiding strips are placed symmetrically with respect to an imaginary central line between the two strips; and that is, the apex angles of the cross sections of the first-order flow guiding columns 122 of the first first-order flow guiding strip and the apex angles of the cross sections of the first-order flow guiding columns 123 of the second first-order flow guiding strip are opposing.

The chip provided by the present disclosure may be used to enrich and sort the circulating tumor cells in peripheral blood. Generally, the maximum size of the cells in peripheral blood is between 6 μm to 15 μm. Therefore, the gap between the parallel side surfaces of two adjacent first-order flow guiding columns is 40 μm to 50 μm, which can ensure that all of the circulating tumor cells and other karyocytes in peripheral blood can pass through the first-order flow guiding strips, and be smoothly dispersed.

In the embodiment provided in FIGS. 1 to 4 of the present disclosure, the flow guiding structure comprises two first-order flow guiding strips. In some embodiments, more than two first-order flow guiding strips may be provided as the first fluid guiding structure upstream of the second sample outlet.

In the present disclosure, the structure of the chip main body is not particularly defined. For example, when the chip is formed by 3D printing, the chip main body may be an integral structure.

In order to improve the accuracy of the chip and simplify the manufacturing process, as shown in FIGS. 1 and 4, the chip main body 100 comprises a cover layer 110 and a sorting layer 120, in which the cover layer 110 and the sorting layer 120 are arranged oppositely. A sorting tank is provided on the surface of the sorting layer 120 that faces the cover layer 110, both of the sample inlet 111 and the first sample outlet 112 are formed on the cover layer, and the cover layer 110 seals the sorting tank, so that the cover layer 110 and the sorting layer 120 form the sorting chamber. The top face of the flow guiding structure and the inner surface of the cover layer 110 are connected. The second sample outlet is formed on the sorting layer, and the capturing columns and the first-order flow guiding columns extend from the sorting layer to the cover layer.

In the present disclosure, the cover layer 110 and the sorting layer 120 may be formed by etching. Because the size of the chip is relatively small, the top face of the flow guiding structure and the inner surface of the cover layer 110 are bonded, thereby realizing the fixed connection between the sorting layer 120 and the cover layer 110.

In the present disclosure, the materials of the cover layer and the sorting layer are not particularly defined. For example, the cover layer 110 may be made of glass, and the sorting layer 120 may be made of a silicon substrate.

When the sorting layer is made of a silicon substrate, plasma etching may be used to form on the substrate patterns such as the sorting chamber, the flow guiding structure, the second sample outlets and the capturing structure. Formation of those patterns by plasma etching will be described in later paragraphs.

Figure 10:
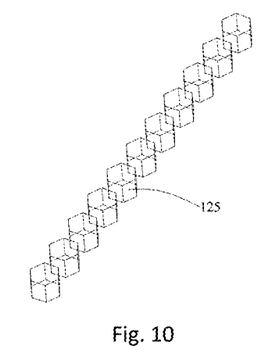
FIG. 10 is a schematic diagram of a second-order flow guiding strip.
Figure 11:
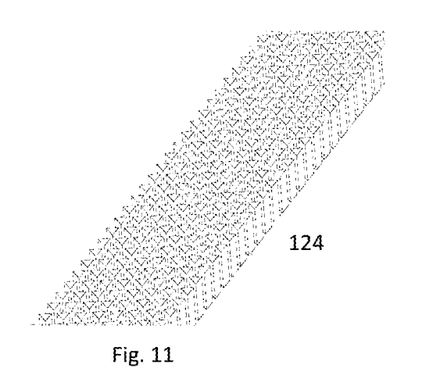
FIG. 11 is a schematic diagram of a capturing structure.

The sorting of the circulating tumor cells may probably use a suction pump. In order to ensure that the chip does not deform in the sorting process, as shown in FIGS. 1 and 4, the chip further comprises a second-order flow guiding strip, which may be referred to as the second fluid guiding structure. The second-order flow guiding strip comprises a plurality of second-order flow guiding columns 125 that are arranged in a line with a gap between adjacent columns. The second-order flow guiding strip may include multiple lines of second-order flow guiding columns 125. The second-order flow guiding strip is provided between the second sample outlets 124 and the capturing structure. As shown in FIG. 10, the second-order flow guiding strip comprises a plurality of second-order flow guiding columns 125 that are arranged as one line; one end of the second-order flow guiding columns 125 is fixed on the bottom wall of the sorting chamber 121, and the other end of the second-order flow guiding columns 125 is connected to the inner surface of the cover layer 110, i.e. each column extends from the sorting layer 120 to the cover layer 110.

As shown in FIG. 3, the first-order flow guiding strips, the second flow guiding strip and the capturing structure partition the sorting chamber 121 into multiple parts, and the parts of the sorting chamber communicate with each other via the gaps between the first-order flow guiding columns 122, 123, the gaps between the second-order flow guiding columns 125 and the gaps between the capturing columns 126.

The second-order flow guiding strip can further support the cover layer 110, and can also smooth the liquid that has been preliminarily sorted, thereby avoiding the liquid that enters the capturing structure from having air bubbles and a dead volume.

In order to increase the contact area with the cover layer 110 and enable the cover layer 110 and the second-order flow guiding columns 125 to be better bonded, the cross section of the second-order flow guiding columns 125 may be a regular hexagon. Because the opposing side surfaces of two adjacent second-order flow guiding columns 125 are parallel, the liquid when flowing through two second-order flow guiding columns 125 can form a steady flow between two adjacent second-order flow guiding columns 125.

In one embodiment, the side length of the regular hexagon is 80 μm to 100 μm, and the distance between the parallel side surfaces of two adjacent second-order flow guiding columns 125 is between 40 μm to 50 μm.

In the present disclosure, the structure of the capturing columns 126, i.e. obstacles 126, is not particularly defined. In the embodiment provided by the present disclosure, the cross section of the capturing columns 126 is a triangle, and the plurality of capturing columns 126 are arranged as an array comprising a plurality of lines of capturing columns. The lines may be arranged such that a capturing column of one line is at an equal distance from two adjacent capturing columns of an adjacent line. In the direction from the sample inlet to the first sample outlet, the gap between two adjacent capturing columns gradually decreases, that is, a distance between the lines of capturing columns decreases in the direction of fluid flow, and the direction of the lines of the capturing columns intersects the longitudinal direction of the sorting chamber.

In one embodiment, the cross section of the capturing columns is an equilateral triangle.

In order to better capture the target cells and enrich the target cells, the array of capturing columns 126 are arranged as 4 to 8 lines. Generally, the maximum size of circulating tumor cells is between 10 μm to 15 μm, and in order to better capture the circulating tumor cells, the distances between two adjacent lines of the capturing columns 126 are 5 μm to 10 μm.

It should be noted that, the cells other than the target cells can pass through the gap between the capturing columns.

In order to facilitate collecting the liquid residual from the sorting, the chip main body 100 may further comprise a back cover layer 130, the back cover layer 130 and the sorting layer 120 are arranged oppositely, and the sorting layer 120 is sandwiched between the back cover layer 130 and the cover layer 110. A collecting tank 131 is provided on the surface of the back cover layer 130 that faces the sorting layer 120, and the collecting tank 131 communicates with the sorting chamber 121 via the second sample outlets 124. The back cover layer 130 is provided with a third sample outlet, and the third sample outlet communicates with the collecting tank 131.

The liquid that has been preliminarily sorted enters the collecting tank 131 via the second sample outlets 124, and is discharged via the third sample outlet.

In the present disclosure, the back cover layer 130 may be made of glass or polydimethylsiloxane (PDMS) materials.

In the embodiment shown in FIG. 4, the back cover layer 130 is provided with two third sample outlets, which are a third sample outlet 132 and a third sample outlet 133.

In one embodiment, the diameter of the third sample outlet may be between 1 mm to 1.1 mm.

In one embodiment, the contour of the collecting tank 131 and the contour of the sorting chamber 121 are the same.

Figure 12:
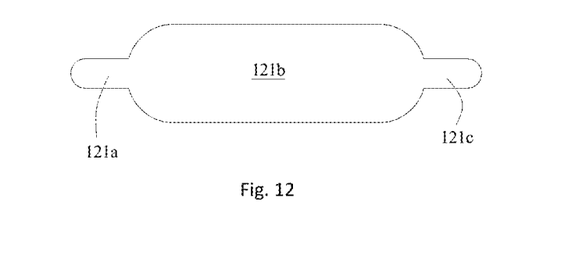
FIG. 12 is a schematic diagram of a sorting chamber.

As shown in FIG. 12, the sorting chamber comprise an inlet guiding tank 121*a*, a sorting tank 121*b* and an outlet guiding tank 121*c*. One end of the inlet guiding tank 121*a* aligns with the sample inlet; the other end of the inlet guiding tank 121*a* communicates with the sorting tank 121*b*; the other end of the outlet guiding tank 121*c* aligns with the first sample outlet; and all of the flow guiding structure, the second sample outlets and the capturing structure are provided within the sorting tank 121*b*.

The sorting tank 121*b* comprises a first cushioning portion, a rectangular portion and a second cushioning portion that are arranged sequentially in the longitudinal direction of the sorting chamber. The inlet guiding tank 121*a* communicates with the first cushioning portion, and the outlet guiding tank 121*c* communicates with the second cushioning portion. The width of the first cushioning portion in the direction from the inlet guiding tank to the rectangular portion gradually increases, and the width of the second cushioning portion in the direction from the rectangular portion to the outlet guiding tank gradually decreases.

In one embodiment, the flow guiding structure comprises two first-order flow guiding strips. The plurality of second sample outlets are arranged as a plurality of lines and a plurality of columns; the length direction of the first-order flow guiding strips and the width direction of the rectangular portion are the same; the direction of the lines of the second sample outlets and the width direction of the rectangular portion are the same; and the direction of the lines of the capturing columns and the width direction of the rectangular portion are the same. In order to enable the liquid to distribute uniformly and flow smoothly, two first-order flow guiding strips, a distribution area of the second sample outlets and the capturing structure are distributed with an equal spacing in the rectangular portion.

Because the outer contour of the collecting tank 131 and the outer contour of the sorting chamber 121 are the same, the collecting tank 131 and the sorting chamber 121 may be formed by the same mask.

In one embodiment, there is provided a sorting system for sorting target cells, comprising a chip as provided above.

The sorting system may further comprise an injecting device such as a micropump or an injection pump, wherein a liquid sample is injected into a sorting chamber of the chip by the injecting device.

In one embodiment, a method for manufacturing a microfluidic cell sorting apparatus is provided, the method comprising: forming a cover layer, the cover layer comprising a first opening as an inlet and a second opening as a first outlet; forming a sorting layer, the sorting layer comprising a first fluid guiding structure, a capturing structure and a second fluid guiding structure formed on a side of a substrate, and a second outlet having an opening through the substrate; and bonding the cover layer with the sorting layer to form a sorting chamber allowing a fluid containing cells to flow from the inlet to the first outlet; wherein the capturing structure for capturing cells is formed upstream of the first outlet, the capturing structure comprising an array of obstacles extending through the sorting chamber in a lateral direction with respect to the fluid flow; and wherein a gap between two adjacent obstacles is equal to or greater than the opening of the second outlet.

Figure 13:
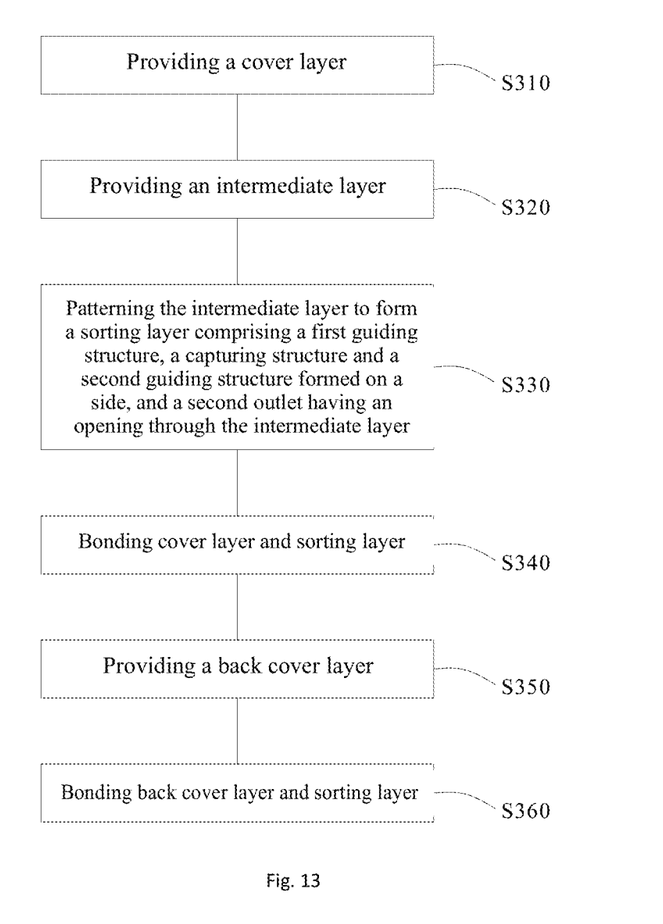
FIG. 13 is a schematic flow chart for manufacturing a chip main body.

Particularly, as shown in FIG. 13, the manufacturing method may comprise:

in Step S310, providing a cover layer, wherein the cover layer comprises a sample inlet and a first sample outlet;

in Step S320, providing an intermediate layer;

in Step S330, patterning the intermediate layer to form a sorting layer, the sorting layer comprising a first fluid guiding structure, a capturing structure and a second fluid guiding structure formed on a side of intermediate layer, and a second sample outlet having an opening through the intermediate layer, wherein the first fluid guiding structure, the second sample outlet and the capturing structure are arranged sequentially in the direction of fluid flow, the capturing structure comprises an array of obstacles extending through the sorting chamber in a lateral direction with respect to the fluid flow, and a gap between two adjacent obstacles is equal to or greater than the opening of the second sample outlet; and in Step S340, aligning and bonding the cover layer and the sorting layer to form the sorting chamber, both of the sample inlet and the first sample outlet communicate with the sorting chamber, and the first fluid guiding structure, the second sample outlet and the capturing structure are arranged sequentially between the sample inlet and the first sample outlet.

The above microfluidic cell sorting apparatus or the above chip provided by the present disclosure can be obtained by the above manufacturing method. The operation principle and the effects of the microfluidic cell sorting apparatus have been in detail described above, and are not discussed here further.

Figure 14:
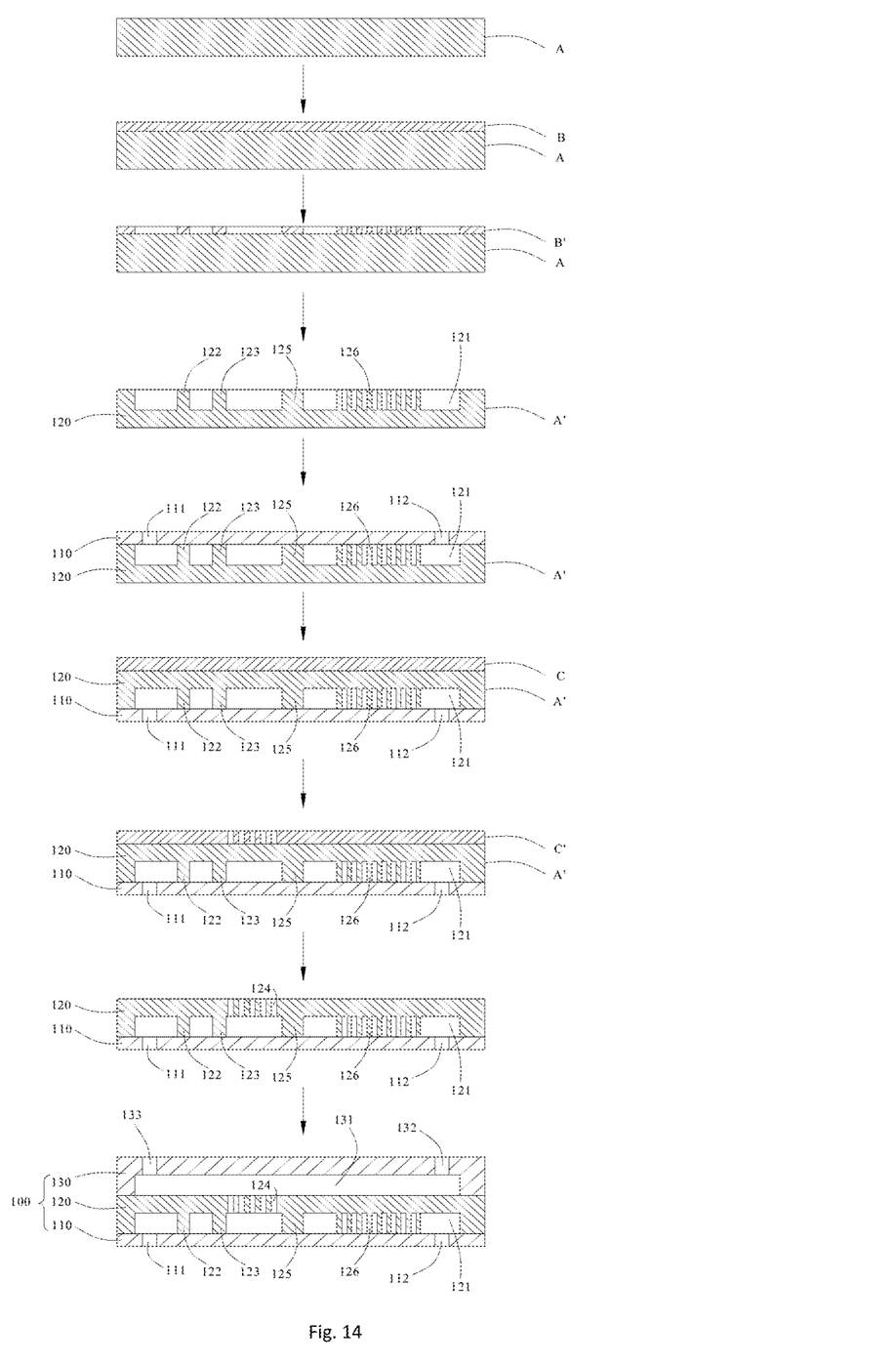
FIG. 14 is a schematic diagram of structures that are obtained in each of the steps of a manufacturing process of the chip main body according to the present disclosure.

In the present disclosure, how to execute Step S330 is not particularly defined. For example, when the material of the intermediate layer is silicon, as an embodiment, as shown in FIG. 14, Step S330 may comprise:

providing a photoresist layer B on the intermediate layer A;

exposing and developing the photoresist layer B, to obtain a mask pattern B', wherein the shape of the mask pattern B' is the identical with the shape of the sorting chamber provided with the flow guiding structure and the capturing structure;

etching the intermediate layer provided with the mask pattern B' by a plasma, to obtain an intermediate structure A' that is provided with the flow guiding structure and the capturing structure;

forming a photoresist layer C on the surface of the intermediate structure A' that has not been patterned;

exposing and developing the photoresist layer C, to obtain a mask pattern C', wherein the mask pattern C' is provided with through holes corresponding to the second sample outlets; and etching the intermediate structure A' provided with the mask pattern C' by a plasma, to obtain the second sample outlets 124, and finally obtain the sorting layer 120.

In the present disclosure, the time when Step S340 is executed is not particularly defined. The cover layer 110 may be bonded to the intermediate structure A' in the process of manufacturing the sorting layer 120, and the cover layer 110 may also be bonded to the sorting layer 120 after the sorting layer 120 is finally obtained.

As shown in FIG. 13, the manufacturing method further comprises:

in Step S350, providing a back cover layer 130, wherein the back cover layer 130 is provided with a collecting tank 131 and a third sample outlet (comprising a third sample outlet 132 and a third sample outlet 133); and in Step S360, aligning and bonding the back cover layer 130 and the sorting layer 120 to form a chamber with a back side of the soring layer 120.

The contour of the collecting tank and the contour of the sorting chamber are the same.

In the present disclosure, the intermediate layer is a silicon wafer, and before the silicon wafer is patterned, the silicon wafer is required to be washed.

In the process of patterning, the thickness of the photoresist layer may be greater than 1μm. After the photoresist layer is formed, optionally, the photoresist layer is firstly pre-heated, and then exposed and developed. Furthermore, after the exposing and developing, optionally, the mask pattern is column-heated, and then plasma etched.

In order to facilitate forming the second sample outlets, optionally, before the photoresist layer C is formed, the side of the surface of the intermediate structure A' that has not been patterned is thinned, and then is formed with the photoresist layer C.

In the present disclosure, how to form the cover layer 110 and how to form the back cover layer 130 are not particularly defined. For example, the cover layer 110 and the back cover layer 130 may be manufactured by molding.

Figure 15:
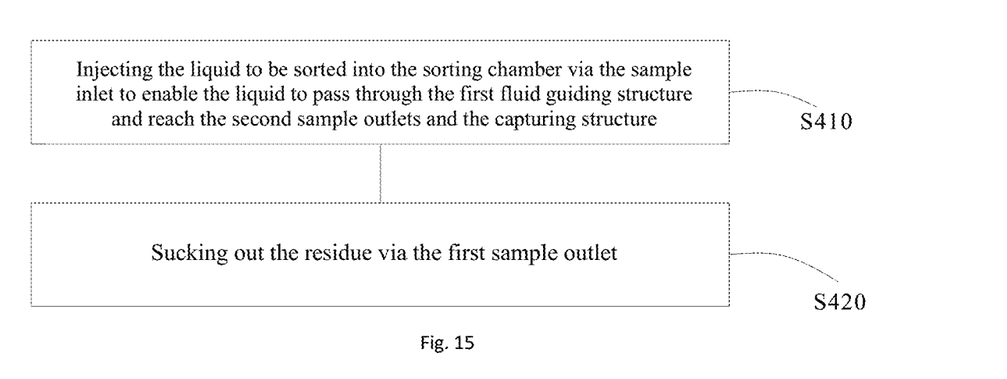
FIG. 15 shows the method for sorting target cells using the chip according to the present disclosure.

In the present disclosure, there is provided a method for sorting target cells by the above chip provided by the present disclosure. As shown in FIG. 15, the method comprises:

in Step S410, injecting the liquid to be sorted into the sorting chamber via the sample inlet to enable the liquid to pass through the first fluid guiding structure and reach the second sample outlets and the capturing structure; and in Step S420, sucking out the residue via the first sample outlet.

As stated above, after the liquid to be sorted is injected into the sorting chamber, the flow of the liquid that enters the sorting chamber is regulated by the pressure and the flow guiding structure, so the liquid can be evenly distributed within the sorting chamber. By preliminary sorting by the second sample outlets to separate the cells of the relatively small volumes and the liquid, the flow resistance in the sorting chamber can be reduced to improve the flux of the liquid.

By capturing the target cells of the relatively large size by the capturing structure, the enriching of the target cells can be realized. Furthermore, cells of the relatively small sizes (that is, the residue in the above) can pass through the capturing structure, and are discharged via the first sample outlet 112.

When the liquid to be sorted comprises peripheral blood and the target cells are circulating tumor cells, the method may further comprise the step of pre-treatment before Step S410. Particularly, the step of pre-treatment may comprise: introducing microspheres into the peripheral blood, to obtain the liquid to be sorted.

After introducing the microspheres into the peripheral blood, the microspheres can adhere to the surfaces of the target cells to form target bodies of a larger size, thereby better facilitating the capturing.

As stated above, an injecting device such as a micropump and a syringe pump may be used to inject the liquid to be sorted into the sample inlet, and the flow field distribution of the liquid within the sorting chamber can be regulated by regulating the injection pressure.

Figure 16:
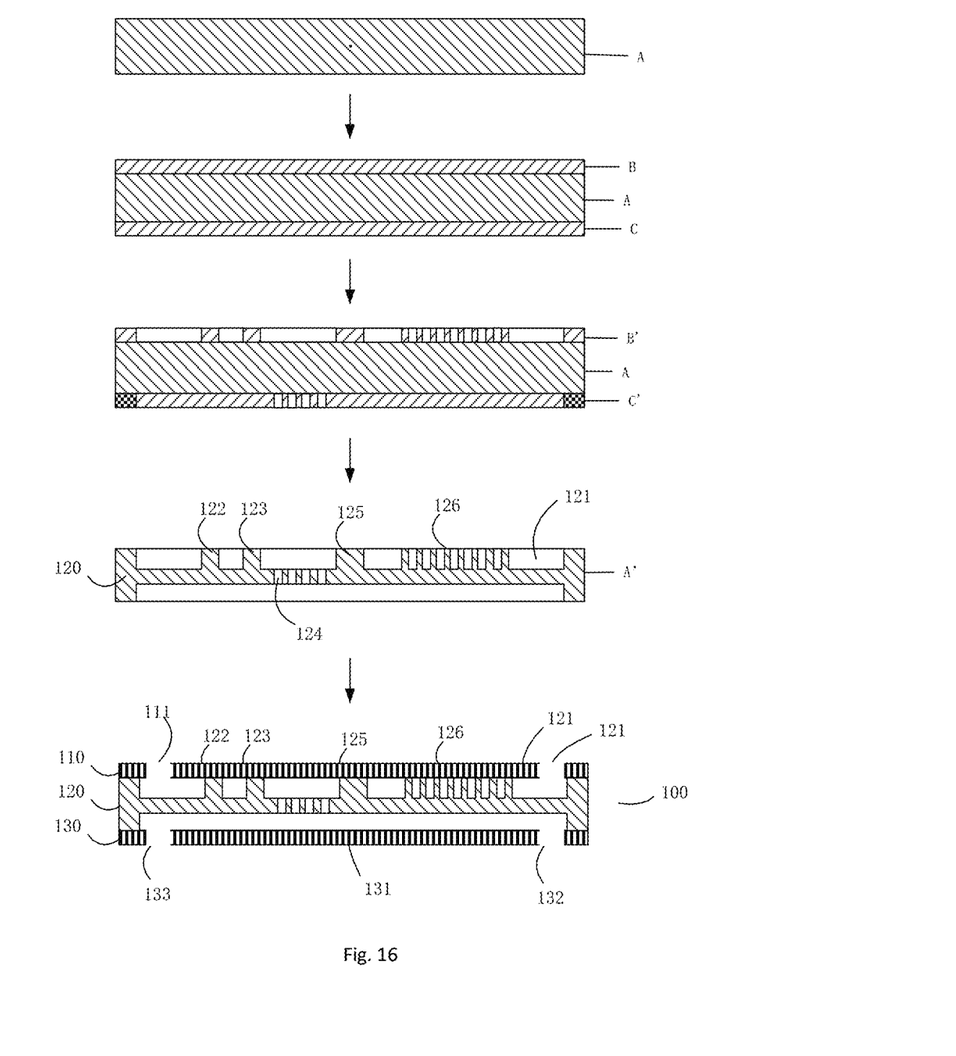
FIG. 16 is a schematic diagram of structures that are obtained in each of the steps of another manufacturing process of the chip main body according to the present disclosure.

FIG. 16 is a schematic diagram of structures that are obtained in each of the steps of another manufacturing process of the chip main body according to the present disclosure. In this embodiment, the sorting layer A may be etched from both side.

In one possible process, as shown in FIG. 16, two photoresist layers B and C are provided on both sides of the intermediate layer A. Subsequently, both photoresist layers B and C are under an exposing and developing process to obtain mask patterns B' and C' respectively. Optionally, the mask pattern C' may be a half tone mask, and the intermediate structure A' may be obtained from a single etching process.

Alternatively, a two-step etching process known in the art may be applied to obtain the intermediate structure A'. For example, this can be achieved by providing an etching protection layer after forming some of the pattern features, before etching some other pattern features.

With the intermediate structure A' having features formed on both sides, identical cover plates may be used as both the cover layer 110 and the back cover layer 130. Therefore, it may possibly result in simpler logistics and significant cost saving in production.

It can be understood that, the above embodiments are merely exemplary embodiments employed in order to interpret the principle of the present disclosure, but the present disclosure is not limited thereto. For a person skilled in the art, without departing from the spirit and essence of the present disclosure, various variations and improvements can be made, and those variations and improvements are deemed to fall within the protection scope of the present disclosure.

The invention claimed is:

1. A microfluidic particle sorting apparatus for capturing targets from fluid containing the targets, comprising:
   an inlet for receiving the fluid;
   a sorting chamber allowing the fluid to flow through;
   a first outlet for discharging the fluid after flowing through the sorting chamber;
   a capturing structure for capturing the cells, wherein the capturing structure is upstream of the first outlet, and comprises obstacles in an array, each extending through the sorting chamber in a lateral direction with respect to a fluid flow of the fluid; and
   a second outlet upstream of the capturing structure comprising a plurality of openings, wherein an opening of the second outlet is less than a preset value.

2. The microfluidic particle sorting apparatus of claim 1, wherein a gap between two adjacent obstacles is equal to or greater than each opening of the second outlet.

3. The microfluidic particle sorting apparatus of claim 2, wherein the gap between two adjacent obstacles is approximately equal to a size of the targets to be captured.

4. The microfluidic particle sorting apparatus of claim 1, wherein the plurality of opening of the second outlet comprises an array of holes, and the gap between two adjacent obstacles is equal to or greater than a diameter of the holes.

5. The microfluidic particle sorting apparatus of claim 1, wherein the sorting chamber is between a cover layer and a sorting layer opposite to one another, the inlet and the first outlet are arranged in the cover layer, the second outlet is arranged in the sorting layer, and each of the obstacle extends from the sorting layer to the cover layer.

6. The microfluidic particle sorting apparatus of claim 5, further comprising a first fluid guiding structure upstream of the second outlet for smoothing the fluid flow, the first fluid guiding structure comprising a plurality of columns, each extending from the sorting layer to the cover layer.

7. The microfluidic particle sorting apparatus of claim 6, wherein the plurality of columns arranged in lines parallel to each other, a most upstream line partially along a cross section of the sorting chamber lateral to a direction of the fluid flow.

8. The microfluidic particle sorting apparatus of claim 7, wherein a column in a downstream line is located corresponding to a gap in an adjacent upstream line.

9. The microfluidic particle sorting apparatus of claim 7, wherein each column of the most upstream line has side surfaces parallel to the fluid flow and a cross section of each column of the most upstream line has a part of decreasing width in the direction of fluid flow.

10. The microfluidic particle sorting apparatus of claim 9, wherein a distance between opposing side surfaces of adjacent columns of the most upstream line is in a range of 40 µm to 50 µm.

11. The microfluidic particle sorting apparatus of claim 8, wherein a cross section of each column of the remaining lines has a part of increasing width in the direction of fluid flow.

12. The microfluidic particle sorting apparatus of claim 5, further comprising a second fluid guiding structure downstream of the second outlet and upstream of the capturing structure for smoothing the fluid flow toward the capturing structure, the second fluid guiding structure comprising a second line of columns, each extending from the sorting layer to the cover layer.

13. The microfluidic particle sorting apparatus of claim 1, wherein the array of obstacles comprises a plurality of lines of obstacles and the lines are arranged such that an obstacle of one line is at an equal distance from two adjacent obstacles of an adjacent line.

14. The microfluidic particle sorting apparatus of claim 13, wherein each obstacle has a triangular cross section and a vertex of the triangle points away from the direction of the fluid flow.

15. The microfluidic particle sorting apparatus of claim 5, further comprising a back cover layer opposite to the sorting layer forming a second chamber with a back side of the sorting layer, wherein the sorting layer is sandwiched between the cover layer and the back cover layer, and at least one third outlet is on the back cover layer.

* * * * *